United States Patent
Ouimette et al.

(10) Patent No.: US 9,247,742 B2
(45) Date of Patent: Feb. 2, 2016

(54) SYNERGISTIC FUNGICIDAL COMPOSITIONS

(71) Applicant: Dow AgroSciences LLC, Indianapolis, IN (US)

(72) Inventors: David Ouimette, Carmel, IN (US); Richard K. Mann, Franklin, IN (US); John Todd Mathieson, Brownsburg, IN (US); Olavo Correa da Silva, Guacu (BR)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/142,756

(22) Filed: Dec. 28, 2013

(65) Prior Publication Data

US 2014/0187508 A1 Jul. 3, 2014

Related U.S. Application Data

(60) Provisional application No. 61/747,475, filed on Dec. 31, 2012.

(51) Int. Cl.
*A61K 31/70* (2006.01)
*A01N 43/24* (2006.01)

(52) U.S. Cl.
CPC .................. *A01N 43/24* (2013.01)

(58) Field of Classification Search
CPC ....... A01N 53/00; A01N 43/40; A01N 43/90; A01N 43/54; A01N 43/80; A01N 43/16; A01N 43/24

See application file for complete search history.

(56) References Cited

U.S. PATENT DOCUMENTS

| 5,276,038 A | 1/1994 | Takasugi et al. |
| 6,953,807 B2 | 10/2005 | Hutin et al. |
| 2004/0110777 A1 | 6/2004 | Annis et al. |
| 2004/0192924 A1 | 9/2004 | Meyer et al. |
| 2010/0137376 A1* | 6/2010 | Komori et al. ................ 514/348 |
| 2011/0082160 A1 | 4/2011 | Owen et al. |
| 2011/0166109 A1 | 7/2011 | Andersch et al. |

OTHER PUBLICATIONS

PCT/US2013/078511 filed Dec. 31, 2013, International Search Report dated Apr. 24, 2014.

* cited by examiner

*Primary Examiner* — Elli Peselev
(74) *Attorney, Agent, or Firm* — C. W. Arnett; Andrews Kurth L.L.P

(57) ABSTRACT

A synergistic fungicidal mixture contains a fungicidally effective amount of a compound of Formula I and at least one fungicide selected from the group consisting of tricyclazole, azoxystrobin, carpropamid, probenazole, kasugamycin, and boscalid.

8 Claims, No Drawings

SYNERGISTIC FUNGICIDAL COMPOSITIONS

CROSS-REFERENCE TO RELATED APPLICATIONS

This application claims the benefit of U.S. Provisional Patent Application Ser. No. 61/747,475 filed Dec. 31, 2012, which is expressly incorporated by reference herein.

FIELD OF THE INVENTION

This invention concerns a synergistic fungicidal composition containing a fungicidally effective amount of a compound of Formula I and at least one fungicide selected from the group consisting of tricyclazole, azoxystrobin, carpropamid, probenazole, kasugamycin, and boscalid.

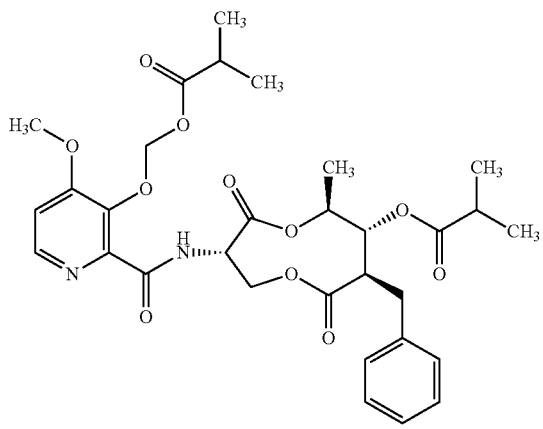

(1)

BACKGROUND AND SUMMARY OF THE INVENTION

Rice is the staple food crop for a large part of the human population in the world today. A crop failure, for any reason, poses a real threat of starvation. Rice blast, caused by a fungus (*Magnaporthe oryzae*; anamorph: *Pyricularia oryzae*) is by far the most important disease of the many diseases that attack rice. The fungus causes lesions to form on leaves, stems, peduncles, panicles, seeds, and even roots. So great is the potential threat for crop failure from this disease that it has been ranked among the most important plant diseases of them all. The rice blast fungus is found wherever rice is grown and is a major threat. Each year it is estimated to destroy enough rice to feed more than 60 million people. Failures of entire rice crops have resulted directly from rice blast epidemics. There is a need for more effective agents for protecting plants, including rice, from damage caused by this pathogen.

Fungicides are compounds, of natural or synthetic origin, which act to protect plants against damage caused by fungi. Current methods of agriculture rely heavily on the use of fungicides. In fact, some crops cannot be grown usefully without the use of fungicides. The use of fungicides allows a grower to increase the yield and the quality of the crop and consequently, increase the value of the crop. In most situations, the increase in value of the crop is worth at least three times the cost of the use of the fungicide.

Unfortunately, no one fungicide is useful in all situations and repeated usage of a single fungicide frequently leads to the development of resistance to that and related fungicides. Consequently, research is being conducted to produce fungicides and combinations of fungicides that are safer, that have better performance, that require lower dosages, that are easier to use, and that cost less. Combinations are also being studied that produce synergism, i.e., the activity of two, or more, compounds exceeds the activities of the compounds when used alone.

It is an object of this invention to provide synergistic compositions comprising fungicidal compounds. It is a further object of this invention to provide processes that use these synergistic compositions.

In one embodiment the invention pertains to a synergistic fungicidal mixture comprising a fungicidally effective amount of a compound of Formula I and at least one fungicide selected from the group consisting of tricyclazole, azoxystrobin, carpropamid, probenazole, kasugamycin, and boscalid

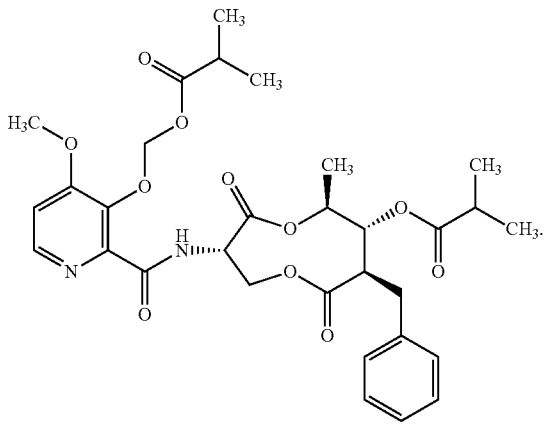

(1)

Advantageously, the synergistic compositions comprising tricyclazole, probenazole, carpropamid, and/or kasugamycin with Formula I are capable of preventing or curing, or both, rice disease caused by, for example, *Magnaporthe oryzae*. Similarly, the synergistic compositions comprising azoxystrobin and/or boscalid with Formula I are capable of preventing or curing, or both, rice disease caused by a wide range of fungi including, for example, *Basidiiomycetes* and/or *Ascomycetes*. In accordance with this invention, synergistic compositions are provided along with methods for their use.

DETAILED DESCRIPTION OF THE INVENTION

The present invention concerns a synergistic fungicidal mixture comprising a fungicidally effective amount of a compound of Formula I and at least one fungicide selected from the group consisting of tricyclazole, azoxystrobin, carpropamid, probenazole, kasugamycin, and boscalid.

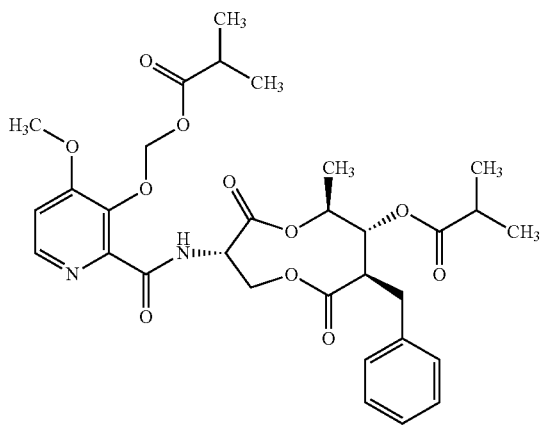

(1)

As used herein, the term "fungicidally effective amount" is synonymous with the phrase "amount effective to control or reduce fungi" and is used in relation to a fungicidal composition in an amount that will kill or materially inhibit the growth, proliferation, division, reproduction, or spread of fungus.

Tricyclazole is the common name for 5-methyl-1,2,4-triazolo[3,4-b]benzothiazole. Its fungicidal activity is described in *The Pesticide Manual*, Fourteenth Edition, 2006. Tricyclazole is a commercial fungicide used to control rice blast.

Azoxystrobin is the common name for methyl (αE)-2-[[6-(2-cyanophenoxy)-4-pyrimidinyl]oxy]-α-(methoxymethylene)benzeneacetate. Its fungicidal activity is described in *The Pesticide Manual*, Fourteenth Edition, 2006. Azoxystrobin controls a variety of pathogens at application rates between 100 and 375 grams/hectare (g/ha).

Carpropamid is the common name for 2,2-dichloro-N-[1-(4-chlorophenyl)ethyl]-1-ethyl-3-methylcyclopropanecarboxamide. Its fungicidal activity is described in *The Pesticide Manual*, Fourteenth Edition, 2006. Carpropamid is a commercial fungicide used to control rice blast.

Probenazole is the common name for 3-(2-propenyloxy)-1,2-benzisothiazole 1,1-dioxide. Its fungicidal activity is described in *The Pesticide Manual*, Fourteenth Edition, 2006. Probenazole is the active ingredient of Oryzemate, an agrochemical which is used to control rice blast. Probenazole is a "plant activator" that protects plants by activating their defense mechanisms.

Kasugamycin is the common name for 3-O-[2-amino-4-[(carboxylminomethyl)amino]-2,3,4,6-tetradeoxy-α-D-arabino-hexopyranosyl]-D-chiro-inositol. Its fungicidal activity is described in *The Pesticide Manual*, Fourteenth Edition, 2006. Kasugamycin is an aminoglycoside antibiotic produced by a bacterium of the genus *Streptomyces*, which is used as a fungicide for controlling rice blast, as well as bacterial infections.

Boscalid is the common name for 2-chloro-N-(4'-chloro[1,1'-biphenyl]-2-yl)-3-pyridinecarboxamide. Its fungicidal activity is described in *The Pesticide Manual*, Fourteenth Edition, 2006. Boscalid provides control of powdery mildew, *Alternaria* spp., *Botrytis* spp., *Sclerotinia* spp. and *Monilia* spp. on a range of fruit and vegetables.

In the composition of this invention, the weight ratio of the compound of Formula I to tricyclazole at which the fungicidal effect is synergistic lies within the range of between about 1:20 and about 4:1. The weight ratio of the compound of Formula I to azoxystrobin at which the fungicidal effect is synergistic lies within the range of between about 1:20 and about 4:1. The weight ratio of the compound of Formula I to carpropamid at which the fungicidal effect is synergistic lies within the range of between about 1:20 and about 4:1. The weight ratio of the compound of Formula I to probenazole at which the fungicidal effect is synergistic lies within the range of between about 1:125 and about 1:2. The weight ratio of the compound of Formula I to kasugamycin at which the fungicidal effect is synergistic lies within the range of between about 1:250 and about 1:1. The weight ratio of the compound of Formula I to boscalid at which the fungicidal effect is synergistic lies within the range of between about 1:1000 and about 1:60.

The rate at which the synergistic composition is applied will depend upon the specific composition, particular type of fungus to be controlled, the degree of control required and the timing and/or the method of application. In general, the composition of the invention can be applied at an application rate of between about 50 grams per hectare (g/ha) and about 2300 g/ha based on the total amount of active ingredients in the composition. Generally, tricyclazole may be applied at a rate between about 100 g/ha and about 300 g/ha and the compound of Formula I may be applied at a rate between about 100 g/ha and about 300 g/ha. Azoxystrobin may be applied at a rate between about 50 g/ha and about 250 g/ha and the compound of Formula I may be applied at a rate between about 100 g/ha and about 300 g/ha. Carpropamid may be applied at a rate between about 100 g/ha and about 300 g/ha and the compound of Formula I may be applied at a rate between about 100 g/ha and about 300 g/ha. Probenazole may be applied at a rate between about 200 g/ha and about 400 g/ha and the compound of Formula I may be applied at a rate between about 100 g/ha and about 300 g/ha. Kasugamycin may be applied at a rate between about 200 g/ha and about 400 g/ha and the compound of Formula I may be applied at a rate between about 100 g/ha and about 300 g/ha. Boscalid may be applied at a rate between about 50 g/ha and about 350 g/ha and the compound of Formula I may be applied at a rate between about 100 g/ha and about 300 g/ha.

The components of the synergistic mixture of the present invention can be applied either separately or as part of a multipart fungicidal system.

The synergistic mixture of the present invention can be applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, Reynoutria sachalinensis extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

The compositions of the present invention are preferably applied in the form of a formulation comprising a composition of a compound of Formula I and at least one fungicide selected from the group consisting of tricyclazole, azoxystrobin, carpropamid, probenazole, kasugamycin, and boscalid, together with a phytologically acceptable carrier if desired.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of a synergistic composition.

The formulations that are applied most often are aqueous suspensions or emulsions. Either such water-soluble, water suspendable, or emulsifiable formulations are solids, usually known as wettable powders, or liquids, usually known as emulsifiable concentrates, aqueous suspensions, or suspension concentrates. The present invention contemplates all vehicles by which the synergistic compositions can be formulated for delivery and use as a fungicide.

As will be readily appreciated, any material to which these synergistic compositions can be added may be used, provided they yield the desired utility without significant interference with the activity of these synergistic compositions as antifungal agents.

Wettable powders, which may be compacted to form water dispersible granules, comprise an intimate mixture of the synergistic composition, a carrier and agriculturally acceptable surfactants. The concentration of the synergistic composition in the wettable powder is usually from about 10% to about 90% by weight, more preferably about 25% to about 75% by weight, based on the total weight of the formulation. In the preparation of wettable powder formulations, the synergistic composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the synergistic composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the synergistic composition comprise a convenient concentration, such as from about 10% to about 50% by weight, in a suitable liquid, based on the total weight of the emulsifiable concentrate formulation. The components of the synergistic compositions, jointly or separately, are dissolved in a carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the synergistic compositions. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the components of the synergistic combination either together or separately, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The synergistic composition may also be applied as granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the synergistic composition in a suitable solvent and applying it to a granular carrier which has been preformed to the appropriate particle size, in the range of from about 0.5 to about 3 mm. Such formulations may also be prepared by making a dough or paste of the carrier and the synergistic composition, and crushing and drying to obtain the desired granular particle.

Dusts containing the synergistic composition are prepared simply by intimately mixing the synergistic composition in powdered form with a suitable dusty agricultural carrier, such as, for example, kaolin clay, ground volcanic rock, and the like. Dusts can suitably contain from about 1% to about 10% by weight of the synergistic composition/carrier combination.

The formulations may contain agriculturally acceptable adjuvant surfactants to enhance deposition, wetting and penetration of the synergistic composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that can comprise at least 1% by weight of one or more of the synergistic compositions with another pesticidal compound. Such additional pesticidal compounds may be fungicides, insecticides, nematocides, miticides, arthropodicides, bactericides or combinations thereof that are compatible with the synergistic compositions of the present invention in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from 1:100 to 100:1.

The present invention includes within its scope methods for the control or prevention of fungal attack. These methods comprise applying to the locus of the fungus, or to a locus in which the infestation is to be prevented (for example applying to rice plants), a fungicidally effective amount of the synergistic composition. The synergistic composition is suitable for treatment of various plants at fungicidal levels, while exhibiting low phytotoxicity. The synergistic composition is useful in a protectant or eradicant fashion. The synergistic composition may be applied by any of a variety of known techniques, either as the synergistic composition or as a formulation comprising the synergistic composition. For example, the synergistic compositions may be applied to the roots, seeds or foliage of plants for the control of various fungi, without damaging the commercial value of the plants. The synergistic composition may be applied in the form of any of the generally used formulation types, for example, as solutions, dusts, wettable powders, flowable concentrates, or emulsifiable concentrates. These materials are conveniently applied in various known fashions.

The synergistic composition has been found to have significant fungicidal effect particularly for agricultural use. The synergistic composition is particularly effective for use with agricultural crops and horticultural plants. In particular, the synergistic compositions comprising tricyclazole, probenazole, carpropamid, and/or kasugamycin with Formula I are capable of preventing or curing, or both, rice disease caused by, for example, *Magnaporthe oryzae*. Similarly, the synergistic compositions comprising azoxystrobin and/or boscalid with Formula I are capable of preventing or curing, or both, rice disease caused by a wide range of fungi including, for example, *Basidiiomycetes* and/or *Ascomycetes*.

The synergistic compositions have a broad range of efficacy as a fungicide. The exact amount of the synergistic composition to be applied is dependent not only on the relative amounts of the components, but also on the particular action desired, the fungal species to be controlled, and the stage of growth thereof, as well as the part of the plant or other product to be contacted with the synergistic composition. Thus, formulations containing the synergistic composition may not be equally effective at similar concentrations or against the same fungal species.

The synergistic compositions are effective in use with plants in a disease inhibiting and phytologically acceptable amount. The term "disease inhibiting and phytologically acceptable amount" refers to an amount of the synergistic composition that kills or inhibits the plant disease for which control is desired, but is not significantly toxic to the plant. This amount will generally be from about 1 to about 1000 ppm, with about 2 to about 500 ppm being preferred. The exact concentration of synergistic composition required varies with the fungal disease to be controlled, the type of formulation employed, the method of application, the particular plant species, climate conditions, and the like. A suitable application rate for the synergistic composition typically corresponds to about 0.10 to about 4 pounds/acre (about 0.1 to 0.45 grams per square meter $g/m^2$).

The present compositions can be applied to fungi or their locus by the use of conventional ground sprayers, granule applicators, and by other conventional means known to those skilled in the art.

The following examples are provided to further illustrate the invention. They are not meant to be construed as limiting the invention.

EXAMPLES

Trial 1. Evaluation of Protectant Activity of Fungicide Mixtures vs. Rice Blast caused by *Magnaporthe oryzae*; anamorph: *Pyricularia oryzae*.

For the mixture studies with compound of Formula I: Treatments consisted of fungicides, including a compound of Formula I, tricyclazole, azoxystrobin, carpropamid, probenazole, kasugamycin, and boscalid, applied either individually or as two-way mixtures with a compound of Formula I. Technical grades of materials were dissolved in acetone to make stock solutions, which were then used to perform three-fold dilutions in acetone either for each individual fungicide component or for the two-way mixtures. Desired fungicide rates were obtained after mixing dilutions with nine volumes of water containing 110 parts per million (ppm) Triton X-100. Ten mL fungicide solutions were applied onto six pots of plants using an automated booth sprayer, which utilized two 6218-1/4 JAUPM spray nozzles operating at 20 pounds per square inch (psi) set at opposing angles to cover both leaf surfaces. All sprayed plants were allowed to air dry prior to further handling. Control plants were sprayed in the same manner with the solvent blank. One day after compound application, plants were inoculated with a *M. oryzae* spore suspension (1×106 spores/ml) and then placed in a 22° C. dew room for 2 days to allow for infection to occur. The plants were then moved to a greenhouse maintained at 24° C. for 8 days to allow for disease symptoms to develop.

When disease reached 40 to 100% on the control plants, infection levels were assessed on treated plants visually and scored on a scale of 0 to 100 percent. Percentage of disease control was then calculated using the ratio of disease on treated plants relative to control plants.

Colby's equation was used to determine the fungicidal effects expected from the mixtures. (See Colby, S. R., Calculation of the synergistic and antagonistic response of herbicide combinations. *Weeds* 1967, 15, 20-22.)

The following equation was used to calculate the expected activity of mixtures containing two active ingredients, A and B:

$$\text{Expected} = A + B - (A \times B / 100)$$

A=observed efficacy of active component A at the same concentration as used in the mixture;
B=observed efficacy of active component B at the same concentration as used in the mixture.

Representative synergistic interactions, including application rates employed and resulting disease control of rice blast is presented in the following Tables 1 and 2.
% DC=Percent disease control
% DC Obs=Percent disease control observed
% DC Exp=Percent disease control expected
Synergism factor=% DC Obs/% DC Exp

TABLE 1

Synergistic interactions of compound I (XDE-777) and other fungicides in 1-day protective *M oryzae* tests.

| Compound A + B | Rate A (ai ppm) | Rate B (ai ppm) | Avg. % Disease | A % DC | B % DC | A + B % DC obs | A + B % DC exp | Synergism factor | >1 synergy |
|---|---|---|---|---|---|---|---|---|---|
| 777 + Azoxystrobin | 0.1 | 1.56 | 50 | 21 | 0 | 40 | 21 | 1.87 | yes |
| 777 + Azoxystrobin | 0.025 | 0.4 | 40 | 0 | 30 | 46 | 30 | 1.54 | yes |
| 777 + Azoxystrobin | 0.1 | 0.1 | 65 | 21 | 19 | 59 | 36 | 1.62 | yes |
| 777 + Azoxystrobin | 0.025 | 0.1 | 65 | 0 | 19 | 43 | 19 | 2.24 | yes |
| 777 + Azoxystrobin | 0.1 | 0.025 | 50 | 21 | 9 | 56 | 28 | 1.98 | yes |
| 777 + Azoxystrobin | 0.025 | 0.025 | 50 | 0 | 9 | 55 | 9 | 6.11 | yes |
| 777 + Azoxystrobin | 0.1 | 1.56 | 50 | 21 | 0 | 51 | 21 | 2.4 | yes |
| 777 + Carpropamid | 0.4 | 0.1 | 65 | 61 | 2 | 65 | 62 | 1.05 | yes |
| 777 + Carpropanid | 0.1 | 0.1 | 65 | 21 | 2 | 65 | 23 | 2.84 | yes |

TABLE 1-continued

Synergistic interactions of compound I (XDE-777) and other fungicides in 1-day protective *M oryzae* tests.

| Compound A + B | Rate A (ai ppm) | Rate B (ai ppm) | Avg. % Disease | A % DC | B % DC | A + B % DC obs | A + B % DC exp | Synergism factor | >1 synergy |
|---|---|---|---|---|---|---|---|---|---|
| 777 + Carpropamid | 0.25 | 0.1 | 65 | 0 | 2 | 65 | 2 | 32.5 | yes |
| 777 + Carpropamid | 0.1 | 0.4 | 50 | 21 | 23 | 54 | 39 | 1.36 | yes |
| 777 + Tricyclazole | 0.025 | 0.4 | 35 | 0 | 23 | 44 | 23 | 1.9 | yes |
| 777 + Tricyclazole | 0.1 | 0.1 | 45 | 21 | 0 | 46 | 21 | 2.17 | yes |
| 777 + Tricyclazole | 0.1 | 0.025 | 25 | 21 | 0 | 39 | 21 | 1.82 | yes |

TABLE 2

Synergistic interactions of compound I (XDE-777) and other fungicides in 1-day curative/protective *M. oryzae* tests.

| Compound A + B | Rate A (ai/ppm) | Rate B (ai/ppm) | Avg. % Disease | A % DC | B % DC | A + B % DC obs | A + B % DC exp | Synergism factor | >1 synergy |
|---|---|---|---|---|---|---|---|---|---|
| 777 + Tricyclazole | 0.4 | 0.1 | 2 | 50 | 71 | 95 | 86 | 1.11 | yes |
| 777 + Tricyclazole | 0.1 | 0.1 | 3 | 28 | 71 | 94 | 79 | 1.19 | yes |
| 777 + Probenazole | 0.1 | 12.5 | 4 | 28 | 78 | 91 | 84 | 1.08 | yes |
| 777 + Probenazole | 1.56 | 3.12 | 2 | 67 | 69 | 95 | 90 | 1.06 | yes |
| 777 + Probenazole | 0.4 | 3.12 | 5 | 50 | 69 | 89 | 85 | 1.05 | yes |
| 777 + Probenazole | 0.1 | 3.12 | 7 | 28 | 69 | 84 | 78 | 1.08 | yes |
| 777 + Kasugamycin | 1.56 | 25 | 1 | 67 | 74 | 98 | 91 | 1.07 | yes |
| 777 + Kasugamycin | 0.4 | 25 | 2 | 50 | 74 | 96 | 87 | 1.10 | yes |
| 777 + Kasugamycin | 0.1 | 25 | 6 | 28 | 74 | 87 | 81 | 1.07 | yes |
| 777 + Kasugamycin | 1.56 | 6.25 | 2 | 67 | 68 | 95 | 89 | 1.06 | yes |
| 777 + Kasugamycin | 0.4 | 6.25 | 4 | 50 | 68 | 91 | 84 | 1.08 | yes |
| 777 + Kasugamycin | 0.1 | 6.25 | 3 | 28 | 68 | 94 | 77 | 1.22 | yes |
| 777 + Kasugamycin | 1.56 | 1.56 | 1 | 67 | 69 | 98 | 90 | 1.09 | yes |
| 777 + Boscalid | 6.25 | 400 | 1 | 81 | 69 | 99 | 94 | 1.05 | yes |
| 777 + Boscalid | 1.56 | 400 | 1 | 67 | 69 | 97 | 90 | 1.08 | yes |
| 777 + Boscalid | 0.4 | 400 | 2 | 50 | 69 | 96 | 85 | 1.14 | yes |
| 777 + Boscalid | 0.1 | 400 | 3 | 28 | 69 | 93 | 78 | 1.2 | yes |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A synergistic fungicidal mixture comprising a fungicidally effective amount of a compound of Formula (1) and at least one fungicide selected from the group consisting of tricyclazole, carpropamid, probenazole, and kasugamycin, wherein the mixture is further characterized by:

(a) a weight ratio of Formula (1) to tricyclazole of between about 1:20 and about 4:1 when the fungicide is tricyclazole;

(b) a weight ratio of Formula (1) to carpropamid of between about 1:20 and about 4:1 when the fungicide is carpropamid;

(c) a weight ratio of Formula (1) to probenazole of between about 1:125 and about 1:2 when the fungicide is probenazole, or (d) a weight ratio of Formula (1) to kasugamycin of between about 1:250 and about 1:1 when the fungicide is kasugamycin (1)

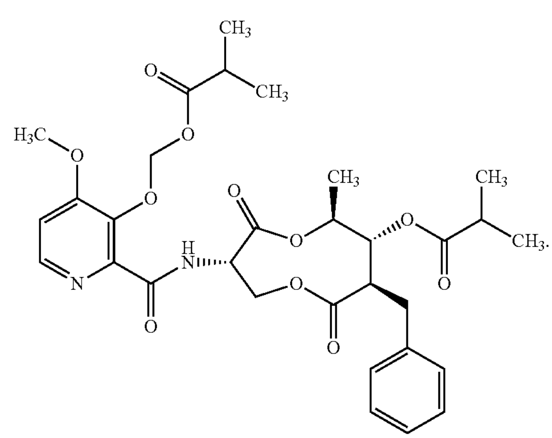

2. The mixture of claim 1 wherein the fungicide is tricyclazole and wherein the weight ratio of Formula (1) to tricyclazole is between about 1:20 and about 4:1.

3. The mixture of claim 1 wherein the fungicide is carpropamid and wherein the weight ratio of Formula (1) to carpropamid is between about 1:20 and about 4:1.

4. The mixture of claim 1 wherein the fungicide is probenazole and wherein the weight ratio of Formula (1) to probenazole is between about 1:125 and about 1:2.

5. The mixture of claim 1 wherein the fungicide is kasugamycin and wherein the weight ratio of Formula (1) to kasugamycin is between about 1:250 and about 1:1.

6. A synergistic fungicidal mixture comprising a fungicidally effective amount of a compound of Formula (1) and boscalid wherein the weight ratio of Compound (1) to boscalid is between about 1:1000 and about 1:60

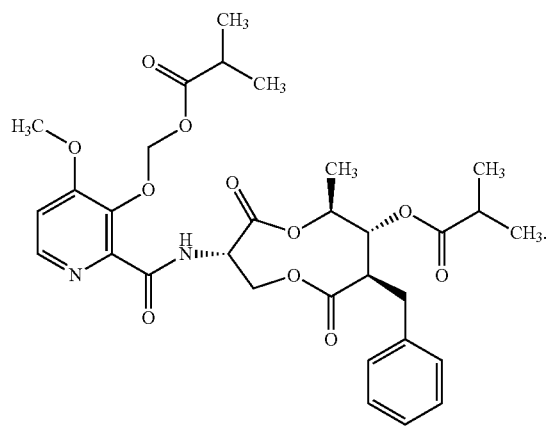

(1)

7. The mixture of claim 1 further comprising an agriculturally acceptable adjuvant or carrier.

8. A method for the control or prevention of fungal attack on a plant, the method comprising: applying a synergistic fungicidal mixture of a fungicidally effective amount of a compound of Formula (1) and at least one fungicide selected from the group consisting of tricyclazole, carpropamid, probenazole, kasugamycin, and boscalid wherein said effective amount is applied to at least one of an area adjacent to the plant, soil adapted to support growth of the plant, a root of the plant, foliage of the plant, and a seed adapted to produce the plant wherein the mixture is further characterized by:

(a) a weight ratio of Formula (1) to tricyclazole of between about 1:20 and about 4:1 when the fungicide is tricyclazole;

(b) a weight ratio of Formula (1) to carpropamid of between about 1:20 and about 4:1 when the fungicide is carpropamid;

(c) a weight ratio of Formula (1) to probenazole of between about 1:125 and about 1:2 when the fungicide is probenazole, (d) a weight ratio of Formula (1) to kasugamycin of between about 1:250 and about 1:1 when the fungicide is kasugamycin, or (e) a weight ratio of Formula (1) to boscalid of between about 1:1000 and about 1:60 when the fungicide is boscalid

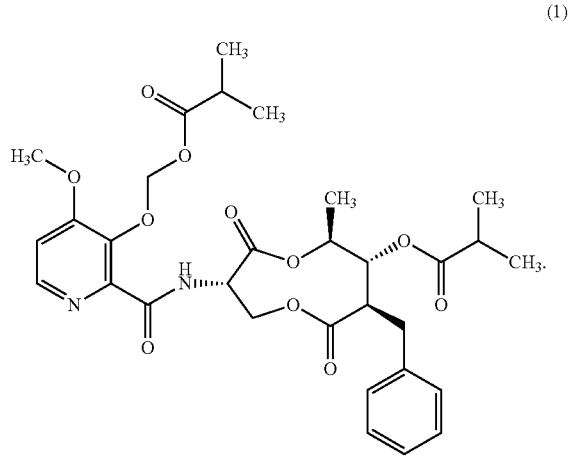 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(1)

* * * * *